(12) United States Patent
Smith

(10) Patent No.: US 9,788,365 B2
(45) Date of Patent: Oct. 10, 2017

(54) APPARATUS AND SYSTEM FOR WARMING INSTRUMENTS

(71) Applicant: Warm, LLC, Puyallup, WA (US)

(72) Inventor: Lowell Jack Smith, Puyallup, WA (US)

(73) Assignee: WARM, Inc., Dana Point, CA (US)

(*) Notice: Subject to any disclaimer, the term of this patent is extended or adjusted under 35 U.S.C. 154(b) by 99 days.

(21) Appl. No.: 14/880,249

(22) Filed: Oct. 11, 2015

(65) Prior Publication Data

US 2016/0095167 A1    Mar. 31, 2016

Related U.S. Application Data

(63) Continuation of application No. 14/497,244, filed on Sep. 25, 2014.

(51) Int. Cl.
| | |
|---|---|
| *H05B 3/06* | (2006.01) |
| *H05B 1/02* | (2006.01) |
| *A61H 37/00* | (2006.01) |
| *H05B 3/40* | (2006.01) |
| *H05B 3/34* | (2006.01) |

(Continued)

(52) U.S. Cl.
CPC .............. *H05B 1/02* (2013.01); *A61B 50/00* (2016.02); *A61B 50/31* (2016.02); *A61H 37/00* (2013.01); *H05B 3/34* (2013.01); *H05B 3/40* (2013.01); *H05B 3/58* (2013.01); *A61B 2050/0016* (2016.02); *A61H 19/00* (2013.01); *A61H 2201/0207* (2013.01); *A61H 2201/0228* (2013.01); *A61H 2201/105* (2013.01);

(Continued)

(58) Field of Classification Search
CPC ... H05B 1/02; H05B 3/40; H05B 3/34; H05B 3/58; A61H 37/00; A61H 2201/0207; A61H 2201/0228; A61H 2201/105; A61H 2201/1207; A61H 2201/5058; A61H 2201/5082; A61H 19/00; A61B 50/00; A61B 50/31; A61B 2050/0016
See application file for complete search history.

(56) References Cited

U.S. PATENT DOCUMENTS

| | | | | |
|---|---|---|---|---|
| 2,617,012 A | * | 11/1952 | Westley | ............... A63B 47/007 |
| | | | | 206/315.91 |
| 3,091,681 A | * | 5/1963 | Mayer | .................. A63B 47/005 |
| | | | | 206/315.91 |

(Continued)

FOREIGN PATENT DOCUMENTS

WO    WO2007000013    1/2007

*Primary Examiner* — Shawntina Fuqua
(74) *Attorney, Agent, or Firm* — Jafari Law Group, Inc.

(57) ABSTRACT

The invention generally involves an apparatus and system for heating or warming instruments. The system includes an electrically heated carrying case for transporting instruments, and an electrically heated vessel for containing a fluid to be used in conjunction with the instruments. The carrying case and the vessel each include: a heating element, one or more sensors (i.e. to maintain a desired temperature) and a circuitry in communication with a user interface for controlling the device's operation. This system facilitates the warming or heating of instruments to a desirable temperature to avoid any undesirable interruptions that may be caused by the discomfort of experiencing a temperature differential upon touching the instrument against the body.

5 Claims, 8 Drawing Sheets

(51) Int. Cl.
  *H05B 3/58*    (2006.01)
  *A61B 50/00*   (2016.01)
  *A61B 50/31*   (2016.01)
  *A61H 19/00*   (2006.01)

(52) U.S. Cl.
  CPC .............. *A61H 2201/1207* (2013.01); *A61H 2201/5058* (2013.01); *A61H 2201/5082* (2013.01)

(56) References Cited

U.S. PATENT DOCUMENTS

| | | |
|---|---|---|
| 3,940,592 A | 2/1976 | Shimizu |
| 5,276,310 A | 1/1994 | Schmidt et al. |
| 5,432,322 A | 7/1995 | Ingram et al. |
| 6,018,143 A | 1/2000 | Check |
| 6,969,831 B1 | 11/2005 | Parker et al. |
| 7,170,035 B2 | 1/2007 | Peterson et al. |
| 8,084,722 B2 | 12/2011 | Haas et al. |
| 8,481,895 B2 | 7/2013 | Taylor et al. |
| 8,785,819 B2 | 7/2014 | Madigan et al. |
| 2012/0048752 A1 | 3/2012 | Madigan et al. |
| 2014/0074196 A1 | 3/2014 | Barnet et al. |

\* cited by examiner

APPARATUS AND SYSTEM FOR WARMING INSTRUMENTS

TECHNICAL FIELD OF THE INVENTION

The present invention relates generally to an apparatus and system for heating or warming instruments, and more specifically, to a transportable apparatus that includes one or more heating components configured to receive and warm instruments typically designed to make contact with the human body. For example, such instruments may include medical or therapeutic instruments, and instruments for use in sexual activities.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

As mentioned above, the instant invention has applications with a wide variety of instruments designed to touch or come in contact with the human body. Although the description below may focus on the use of the present invention for warming instruments specifically designed for use during sexual activities, it is understood that other types of instruments may be warmed by utilizing the present invention. As used in this specification, the term instrument may refer to medical devices, therapeutic devices, devices for use during sexual activities, or any other type of device that is designed to come in contact with the human body. As such, examples of an instrument that may be warmed by utilizing the present invention may include a stethoscope or stethoscope component, an ultrasound transducer, a speculum, therapy stones, a vibrator, a male stimulator, a female stimulator, or any other similar device that is designed to make contact with skin, an orifice, or any body part.

One of the problems typical of any instrument that comes in touch or designed to make contact with the human body, is the discomfort experienced from the temperature differential between the instrument and the user's body. Typically, an instrument that has been left in a room is at room temperature or anywhere between 68-73° F., while the human body is normally 98.6° F. The sudden application of any instrument at a temperature that may be 20-25 degrees cooler, causes the user discomfort. This is a problem for users undergoing medical or therapeutic procedures, or engaging in sexual activities, for example. That is, unless these instruments are heated or warmed prior to their use, the user will experience a discomforting sensation, which typically causes an undesirable interruption prior to or during the activity—for example, involuntary muscle contractions or tensed muscles. With regards to sexual activities, prior interruptions or initial discomfort due to the cold sensation of an instrument or object against the body can cause undesirable distractions and diminish the quality of the experience. Thus, there is a need in the art for providing a means to warm instruments designed to contact the body.

The prior art does not provide an adequate means to properly warm such instruments prior to their use, especially with regards to the latter of the examples mentioned above-instruments or products often referred to as intimacy enhancers. These instruments, such as female or male stimulators, are typically comprised of known configurations utilized for the purposes of increasing sexual stimulation through known methods. It is also known that these instruments consist of structural configurations that are expected and familiar, typically due to their correspondence with the human body. Because the surface area of some instruments may vary in shape, so as to conform to a particular body part or in order to register with a desired orifice, adequately warming each instrument's surface area is challenging. Thus, there is a need in the art for a warming apparatus or system that adequately addresses properly heating or warming different surface areas to suit differently shaped instruments.

Another problem arises when transportation of these instruments is required. For example, it may be required to take a device from one location to another, and it may be desirable to have the device warmed upon arrival- or soon thereafter. In the context of instruments used during sexual activities, it is well known that gatherings occur wherein use of adult toys is desirable. In such circumstances, it is desirable not only to keep the devices warm, but also to keep some level of discretion when transporting these devices. Thus, there is a need in the art for a means to discreetly transport instruments, while providing the instruments warmth prior to their use.

Therefore, there exists a previously unappreciated need for a new and improved apparatus and system that: warms or heats instruments designed to contact the body; adequately addresses properly heating or warming different surface areas to suit differently shaped instruments; and discreetly provides a means of transporting instruments, while providing a means to warm or heat the instruments prior to use.

It is to these ends that the present invention has been developed.

SUMMARY OF THE INVENTION

To minimize the limitations in the prior art, and to minimize other limitations that will be apparent upon reading and understanding the present specification, the present invention describes an apparatus and system for heating or warming instruments, and more specifically, to a transportable apparatus, such as a carrying case or flexible cover with a heating component, which includes one or more heating elements configured to warm up instruments designed to come in contact with the human body. For example, such instruments may include medical or therapeutic instruments or objects, and instruments for use during sexual activities.

An apparatus in accordance with one embodiment of the present invention comprises: a carrying case for containing one or more instruments; one or more heating components coupled to the carrying case and configured to receive and warm the one or more instruments; one or more heating elements contained within the one or more heating components; and circuitry configured to control and supply power to the one or more heating elements.

Another apparatus in accordance with one embodiment of the present invention comprises: an outer housing; an inner housing coupled to the outer housing and configured to receive and warm an instrument; a heating element contained within the inner housing; and circuitry configured to supply power to the heating element, the circuitry for controlling a heat output generated by the heating element.

Yet another apparatus in accordance with one embodiment of the present invention comprises: a carrying case for containing one or more instruments; one or more heating components coupled to the interior of the carrying case and configured to receive and warm the one or more instruments; circuitry configured to control and supply power to the one or more heating components; an interface for connecting the one or more heating components to a power supply; and a control module, including a user interface for manually setting the heat output generated by the one or more heating components, the control module removably attached to the circuitry via a connector situated on the exterior of the carrying case.

An electrically heated vessel, in accordance with one embodiment of the present invention, comprises: a base including a heating component; one or more thermal sensors coupled to the heating component; a circuitry in communication with a user interface for controlling the heating component's operation; a vessel removably coupled to the base, the vessel for containing a fluid; a motor for activating a pump and dispensing the fluid; one or more motion sensors for activating the motor; and a power supply for supplying power to the sensors, motor and heating element.

A system for heating or warming instruments, in accordance with one embodiment of the present invention, comprises: an apparatus including a carrying case for containing one or more instruments; one or more heating components coupled to the interior of the carrying case and configured to receive and warm the one or more instruments; circuitry configured to control and supply power to the one or more heating components; an interface for connecting the one or more heating components to a power supply; and a control module, including a user interface user interface for manually setting the heat output generated by the one or more heating components, the control module removably attached to the circuitry via a connector situated on the exterior of the carrying case; the system further including an electrically heated vessel, including: a base with a heating component; one or more thermal sensors coupled to the heating component; a circuitry in communication with a user interface for controlling the heating component's operation; a vessel removably coupled to the base, the vessel for containing a fluid; a motor for activating a pump and dispensing the fluid; one or more motion sensors for activating the motor; and a power supply for supplying power to the sensors, motor and heating element.

It is an objective of the present invention to provide an apparatus that warms instruments to a desired temperature, for example within range of a normal human body temperature.

It is another objective of the present invention to provide an apparatus that facilitates the transportation of instruments from one location to another, while maintaining the instrument's warmth.

It is yet another objective of the present invention to provide a heating element implemented within the apparatus so that the instruments may be warmed prior to use.

It is yet another objective of the present invention to provide a means to securely transport instruments in a medium that enables a source of warmth prior to using the instruments therein.

It is yet another objective of the present invention to provide a sanitary means of transporting instruments from one location to another.

These advantages and features of the present invention are not meant as limiting objectives, but are described herein with specificity so as to make the present invention understandable to one of ordinary skill in the art.

BRIEF DESCRIPTION OF THE DRAWINGS

Elements in the figures have not necessarily been drawn to scale in order to enhance their clarity and improve understanding of the various embodiments of the invention. Furthermore, elements that are known to be common and well understood to those in the industry are not depicted in order to provide a clear view of the various embodiments of the invention. The drawings that accompany the detailed description can be briefly described as follows.

DETAILED DESCRIPTION OF THE INVENTION

Figure 1:
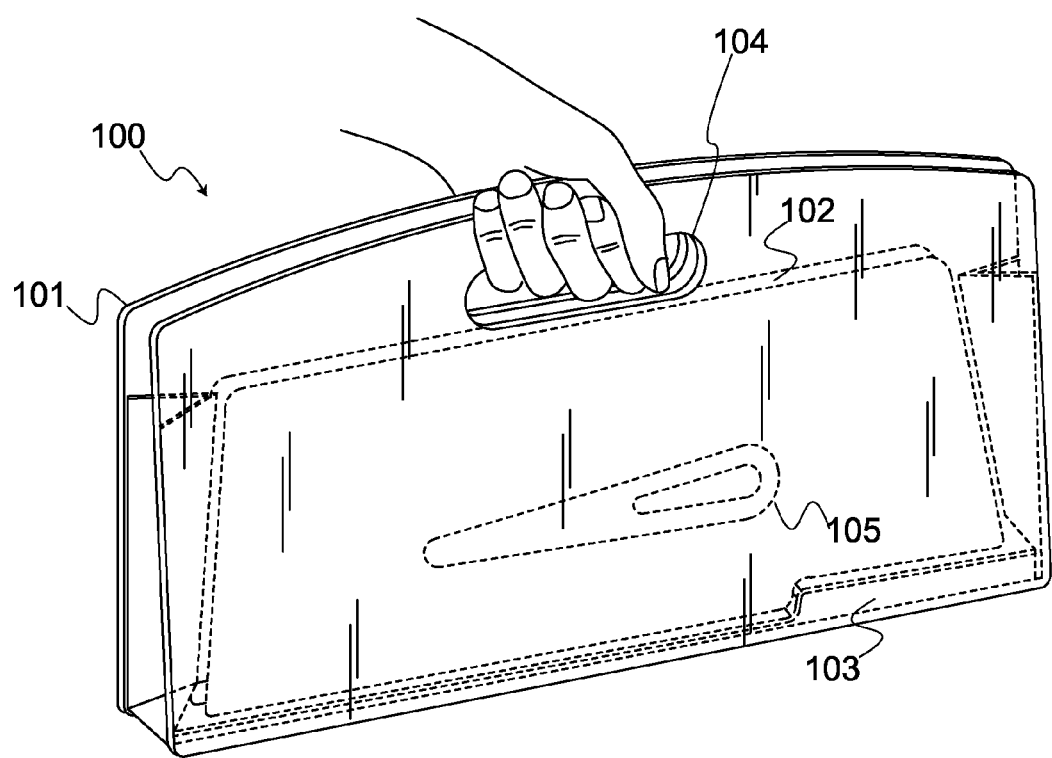
FIG. 1 depicts a perspective view of an apparatus in accordance with one embodiment of the present invention.

In the following discussion that addresses a number of embodiments and applications of the present invention, reference is made to the accompanying figures, which form a part thereof. Depictions are made, by way of illustration, of specific embodiments in which the invention may be practiced; however, it is to be understood that other embodiments may be utilized and changes may be made without departing from the scope of the present invention.

Generally, the invention involves an apparatus and system for heating or warming instruments. More specifically, the invention involves a system that includes a transportable apparatus comprising one or more heating components configured to warm instruments designed to come in contact with the human body. For example, and without limiting the scope of the present invention, such instruments may include medical or therapeutic instruments, and instruments for use in sexual activities. In an exemplary embodiment, the system comprises of two devices: (1) an electrically heated carrying case or flexible cover for transporting instruments, and (2) an electrically heated vessel for containing a fluid to be used in conjunction with the instruments. In such embodiment, the carrying case or flexible cover and the vessel each include: a heating component—the heating component containing a heating element, one or more sensors (i.e. to maintain a desired temperature) and a circuitry in communication with a user interface for controlling the device's operation. This system facilitates the warming or heating of instruments to a desirable temperature so as to make their use a more pleasant experience, and/or avoid any undesirable interruptions that may be caused by the discomfort of experiencing a temperature differential when the instrument comes in contact with the body.

A carrying case or flexible cover in accordance with such embodiment of the present invention may generally include a heating component or inner housing or envelope that encloses the heating element. In exemplary embodiments, the configuration of housing and heating element may be flexible. This flexibility facilitates wrapping the heating element around the surface of an instrument to ensure that substantially an entire surface area of the instrument is covered completely and radiated with adequate heat. In order to supply power to the heating element, a circuitry may be housed within or coupled to the housing, which communicates with a power supply unit that may be coupled to the carrying case or flexible cover via an interface. The interface may rest substantially in an interior of the carrying case, or on a surface of a heating component configured to be wrapped by the flexible cover. The interface may be configured to connect to an external electrical power source such as an adapter, a rechargeable battery, or simply to a garden variety electrical socket. In alternative embodiments the interface may have multiple connectors for connecting with additional heating components that may be configured to register with different types of instruments.

For example, and without deviating from the scope of the present invention, an interface may be configured to connect with a flexible heating element, as well as a rigid heating element. The flexible heating element may be suitable for wrapping around an outer surface area of instruments; the rigid heating element may be suitable for inserting, mating or registering with an inner surface area of an instrument. Furthermore, the carrying case is configured to facilitate the transportation of instruments, so that instruments may be carried from one location to another discreetly, and may be heated or warmed prior to use. Moreover, instruments may be carried in a manner that ensures the instruments are kept sanitary prior to using them for their intended purpose.

An electrically heated vessel, in accordance with such exemplary embodiment of the present invention, may include a body configured to receive a fluid container. The body of the vessel may contain a cavity for housing a heating element and a temperature sensor. A circuitry may provide power to the heating element. A controller may be connected to the circuitry, and in communication with the sensor, to provide a means to control the desired temperature of the fluid inside the fluid container. The fluid container may be a simple fluid container, or a motorized sensor activated fluid container. Once placed within the heated vessel, the fluid container may be warmed or heated so that the fluid is expelled at a desired temperature. The drawings and various views of the figures will help elaborate and explain the different aspects of the invention, which are discussed in greater detail below.

Turning now to the figures, FIG. 1 depicts a perspective view of an apparatus in accordance with one embodiment of the present invention. More specifically, apparatus 100 is depicted being carried by a user, and comprising: carrying case 101, a heating component or housing 102 and interface 103; each component interior to carrying case 101 shown with dotted lines. Additionally, instrument 105 is shown housed within housing 102, presently being transported from one location to another.

Carrying case 101 includes housing 102 and may be constructed of any suitable material such as cloth, plastics, leather, metals or a combination thereof. For example, and without limiting the scope of the present invention, materials for carrying case 101 may include steel, aluminum, wool, linen, nylon, polycarbonate, polyethylene, polypropylene, polyvinyl chloride (PVC), one or more combinations thereof, or any other material that is durable and sturdy enough for transportation. As shown, carrying case 101 may include a handle or support member 104 to facilitate carrying apparatus 100 from one location to another. Furthermore, carrying case 101 may comprise a variety of shapes—rectangular, oblong, or any other suitable configuration that facilitates transportation and storage.

Housing 102 is typically a heating component that houses or implements a heating element. Housing 102 may be flexible and may comprise one or more layers that create an enclosure for housing a heating element (i.e. not shown in FIG. 1, but discussed below with reference to other figures). For example, and without limiting the scope of the present invention, housing 102 may comprise of a first layer configured to house a heating element, and a second layer configured to cover the first layer, so as to form a flexible surface or flexible heating component that can be used to wrap or enclose an instrument such as instrument 105. In exemplary embodiments, housing 102 is a flexible heating component including a first sturdy but flexible layer that houses a heating element, and second layer comprising soft linen that snuggly holds instrument 105 in place. Of course, other configurations and other materials may be implemented without deviating from the scope of the present invention.

Interface 103 may be any type of connection means that facilitates a power supply to the heating element within housing 102. In one embodiment, interface 103 is a power interface. In another embodiment, interface 103 includes an actuator sensor interface. In yet another embodiment, interface 103 includes a connection means for providing a power supply in addition to providing access to a controller and user interface for activating the heating element inside housing 102. Furthermore, interface 103 may facilitate communication of one or more sensors embedded or implemented within housing 103. In yet another embodiment, interface 103 may further implement a rechargeable battery so as to allow operation of heating element 102 during transportation.

As explained above, instrument 105 may be a medical instrument, a therapeutic instrument, an instrument for use in sexual activities, or any other instrument that may benefit from being warmed prior to its use. For example, and without deviating from the scope of the present invention, instrument 105 may be an instrument used during sexual activities. Because it is desirable to warm instrument 105 prior to touching the instrument against the body, instrument 105 may be placed in apparatus 100 and warmed prior to use.

Figure 2:
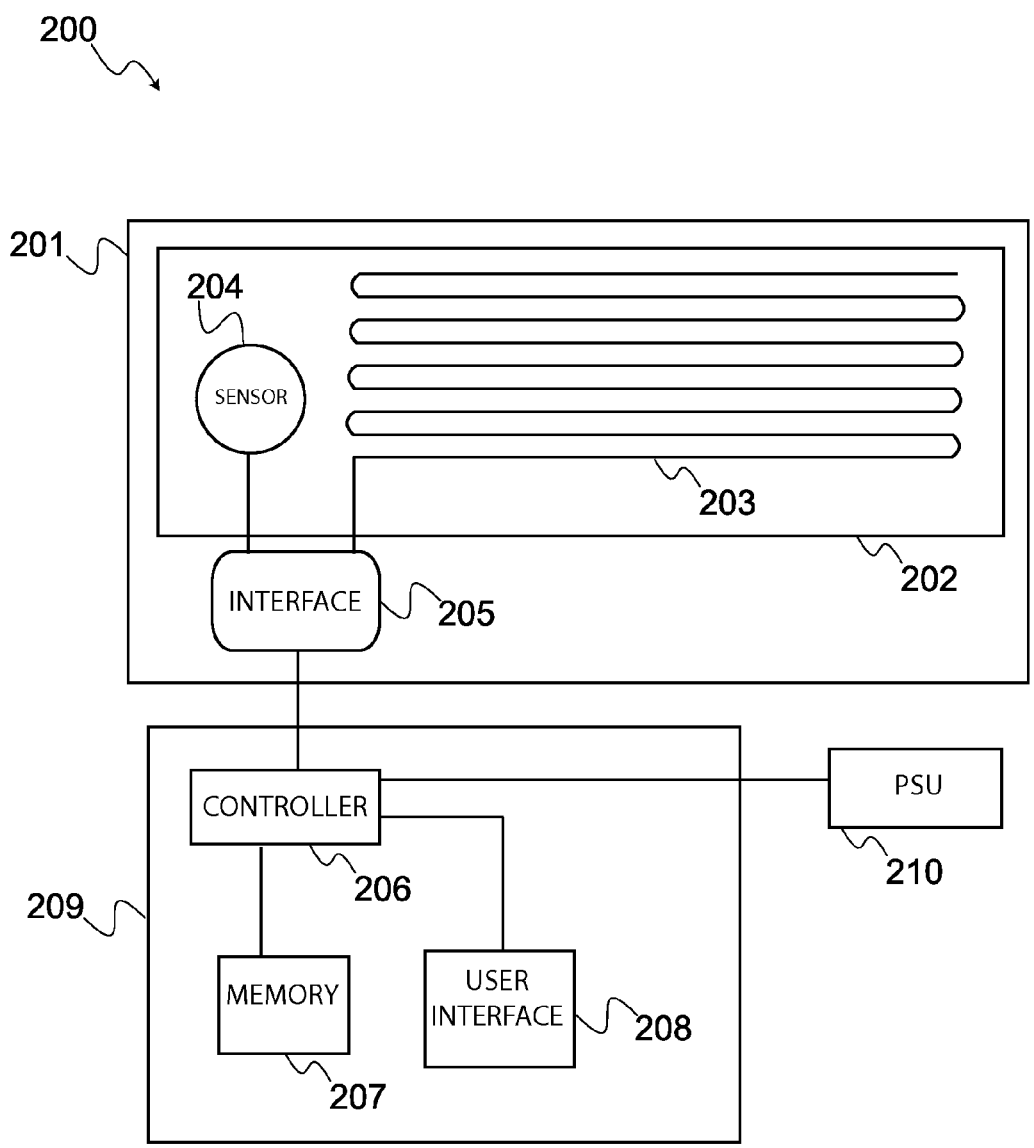
FIG. 2 depicts a diagram showing the various components of one embodiment of the present invention, wherein a single heating component is housed within an outer housing, and wherein an external control module is removably attached to the outer housing via an interface that connects the control module to the heating component.

Now turning to FIG. 2, a diagram showing the various components of one embodiment of the present invention is depicted. More specifically, FIG. 2 shows apparatus 200 comprising outer housing 201, inner housing 202, heating element 203, one or more sensors 204, interface 205, and control module 209. Control module 209 includes a circuitry that comprises controller 206, memory 207, and user interface 208. In order to draw power and supply power to heating element 203, control module 209 may be connected to a power source; in the present case, power supply unit (PSU) 210 is utilized for this purpose.

Outer housing 201 is configured to house or contain one or more components such as a heating component or inner housing 202 and interface 103, as well as any instrument that may be carried or transported within apparatus 200. Outer housing 201 may be constructed of any suitable material that facilitates the transportation of one or more instruments. Outer housing may be constructed of any suitable material such as cloth, plastics, leather, metals or a combination thereof. For example, and without limiting the scope of the present invention, outer housing 201 may be constructed with one or more materials such as steel, aluminum, wool, linen, nylon, polycarbonate, polyethylene, polypropylene, polyvinyl chloride (PVC), or any other material that is durable and sturdy enough for manufacturing an outer housing suitable for transportation. In an exemplary embodiment, outer housing 201 resembles carrying case 101 and may include features similar to luggage or handbags, which may include features such as handles, straps, buttons, zippers, draw strings, hook-and-loop fasteners (e.g. Velcro®), or any combination of features, fasteners, or connectors that facilitate secure containment and transportation of one or more instruments. In another exemplary embodiment, outer housing 201 is a flexible cover with a substantially flat configuration that may be constructed so that outer housing 201 is stretchable and may be wrapped or rolled to enclose one or more instruments within its flat surface area.

Inner housing 202 is a heating component configured to house heating element 203. Inner housing 202 may include one or more layers to provide a secure envelope for containing heating element 203, as well as a layer that is constructed of a soft material suitable for wrapping or snuggly holding an instrument. For example, and without limiting the scope of the present invention, inner housing 202 may include a soft linen layer that preserves (or does not interfere) with the surface area of the instrument contained therein. That is, in exemplary embodiments, inner housing 202 will not scratch or cause undue wear and tear of the instruments housed within apparatus 200. Furthermore, inner housing 202 is typically insulating so that heat generated by heating element 203 is not quickly lost, and instead preserved so as to save the device's energy consumption while keeping the instrument warm inside apparatus 200.

Heating element 203 may be constructed of well known components. For example, and without limiting the scope of the present invention, heating element 203 may include a thin film of heating circuitry that includes commercially available resistor elements for generating a desired temperature range. Heating element 203 typically communicates with control module 209 to receive a power supply for generating heat. Furthermore, heating element rests inside inner housing 202, where it is appropriately secured. In an exemplary embodiment, heating element 203 is flexible so that inner housing 202 may be wrapped around an instrument or folded within outer housing 201. Typically, heating element is contained within one or more layers, securely held in place to prevent undesired shifting and maintain an even heat radiation throughout inner housing 202.

Sensors 204 may be coupled to a circuitry in communication with heating element 203, or may be part of a commercially available heating element that implements temperature sensing capabilities. Typically, sensors 204 are temperature sensors used to prevent overheating, and to provide control module 209 with information pertaining to the temperature within apparatus 200. For example, and without deviating from the scope of the present invention, sensors 204 may provide data to control module 209 in order to keep an instrument at a desired temperature range.

Interface 205 may be any type of connection means that provides a power supply to heating element 203. In one embodiment, interface 205 is a power supply interface. In another embodiment, interface 205 is a power supply and sensing data interface. In yet another embodiment, interface 205 includes a connection means for providing a power supply in addition to providing access to control module 209 for activating and regulating the temperature generated by heating element 203. In other embodiments, interface 205 may further implement a rechargeable battery (not shown) so as to allow operation of heating element 203 during transportation.

Control module 209 may include circuitry that may range or vary in complexity. For example, and without limiting the scope of the present invention, control module 209 may include a circuitry as shown, a simpler circuitry, or much more complex circuitry. As shown, control module 209 comprises controller 206, memory 207, and user interface 208. Control module 209 is the control center for apparatus 200 and may be situated outside of outer housing 201 or inside outer housing 201. In the shown embodiment, control module is coupled to an exterior of outer housing 201 whenever apparatus 200 is actuated. Control module 209 facilitates control of the temperature output of heating element 203 by allowing a user to turn the device on or off, and either setting the device to a pre-set temperature or manually setting the temperature via user input. Control module 209 typically draws power from PSU 210 and supplies an adequate voltage to heating element 203. Furthermore, control module 209 may communicate with one or more sensors 204 in order to maintain the instrument at a desired temperature.

Controller 206 may comprise a single processor, microprocessor, or any other type of processing power suitable for running basic controls for operating apparatus 200. For example, and without limiting the scope of the present invention, controller 206 may be suitable for executing a basic logic, or executable program code, that enables control of the heat generated by heating element 203. To this end, a basic memory, such as memory 207 may be included in the circuitry. Also, control module 209 may include other known electrical components such as safety fuses and switches for enabling a safe operation of apparatus 200. Furthermore, control module 209 may further include user interface 208, which may be a simple dial input device such as a potentiometer, or a more complex input/output device that allows a user to input a desired temperature range for heating element 203.

PSU 210 may be a typical adapter configured to supply an adequate voltage to the circuitry of control module 209 as well as heating element 203. Alternatively, in other embodiments, PSU may be replaced or implemented with a rechargeable battery located within or exterior to outer housing 201. Alternatively PSU 210 may include an adapter—for example and without limiting the scope of the present invention—a USB adapter, a cigarette lighter adapter for a vehicle, or any other type of adapter adapted to supply power to apparatus 200 from a suitable power source.

Figure 3:
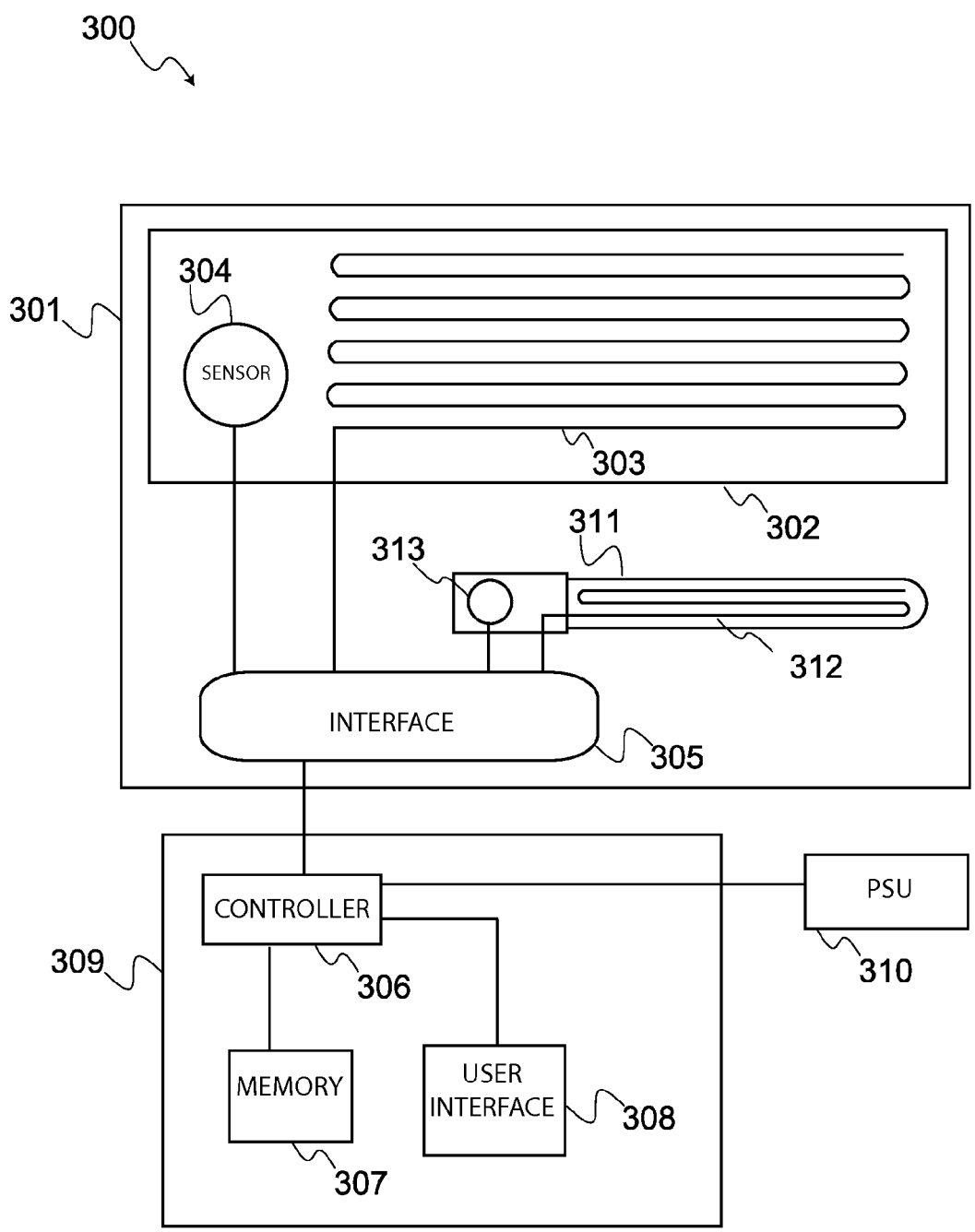
FIG. 3 depicts another diagram showing the various components of another embodiment of the present invention; this embodiment accommodates different types of instruments by implementing more than one heating component configured to mate or register with different instrument types.

FIG. 3 depicts another diagram showing the various components of another embodiment of the present invention; this embodiment accommodates different types of instruments by implementing more than one heating element configured to mate or register with different instrument types. More specifically, apparatus 300 includes similar components as those described in FIG. 2, but adds a few components. For example, apparatus 300 similarly includes outer housing 301, inner housing 302, heating element 303, one or more sensors 304, interface 305, and control module 309. Like apparatus 200, control module 309 of apparatus 300 includes a circuitry that comprises controller 306, memory 307, and user interface 308. In order to draw power and supply power to heating element 303, control module 309 may be connected to a power source; in the present case, power supply unit (PSU) 310.

Apparatus 300 includes additional components, mainly a different interface that is configured to connect to multiple heating components with heating elements, such as heating element 303 and heating element 312. Heating element 312 is housed within a rigid housing 311, which may comprise one or more sensors 313 for reading a temperature output of heating element 312.

Outer housing 301 and inner housing 302 are similar to housings 201 and 202, except that their size may vary in order to accommodate the additional components of apparatus 300 not present in apparatus 200.

Rigid housing 311 is a heating component that may be constructed of plastics or any other rigid material that is suitable for inserting or registering with instruments that have a surface area within a cavity designed to make contact with the human body or body part. An example of one embodiment of rigid housing 311 is shown and discussed with reference to FIG. 4(b). Rigid housing 311 need not be constructed so that it is completely inflexible; however, rigidity may be desirable for the housing to be able to be inserted into an instrument's cavity with easy. Rigid housing 311 houses heating element 312.

Heating elements 303 and 312 may be constructed of well known components similar to heating element 204. For example, and without limiting the scope of the present invention, heating elements 303 and 312 may include a thin film of heating circuitry that includes commercially available resistor elements for generating a desired temperature range. As with heating element 203, heating elements 303 and 312 typically communicate with control module 309 to receive a power supply for generating heat. Furthermore, the heating elements rest inside their respective housings appropriately secured.

Interface 305 is typically suitable for facilitating a power supply to both heating elements 303 and 312. Additionally, interface 205 may be configured to enable communication of any sensor data to and from control module 309 (i.e. between sensors 304, 313, and controller 306).

While the other components of apparatus 300 are similar to those of apparatus 200, described in reference to FIG. 2, the additional components of apparatus 300 typically function similarly but serve the purpose of providing a more effective mechanism for warming certain types of well known instruments. A more detailed discussion of the use of such components is described with reference to the next figures.

Figure 4A:
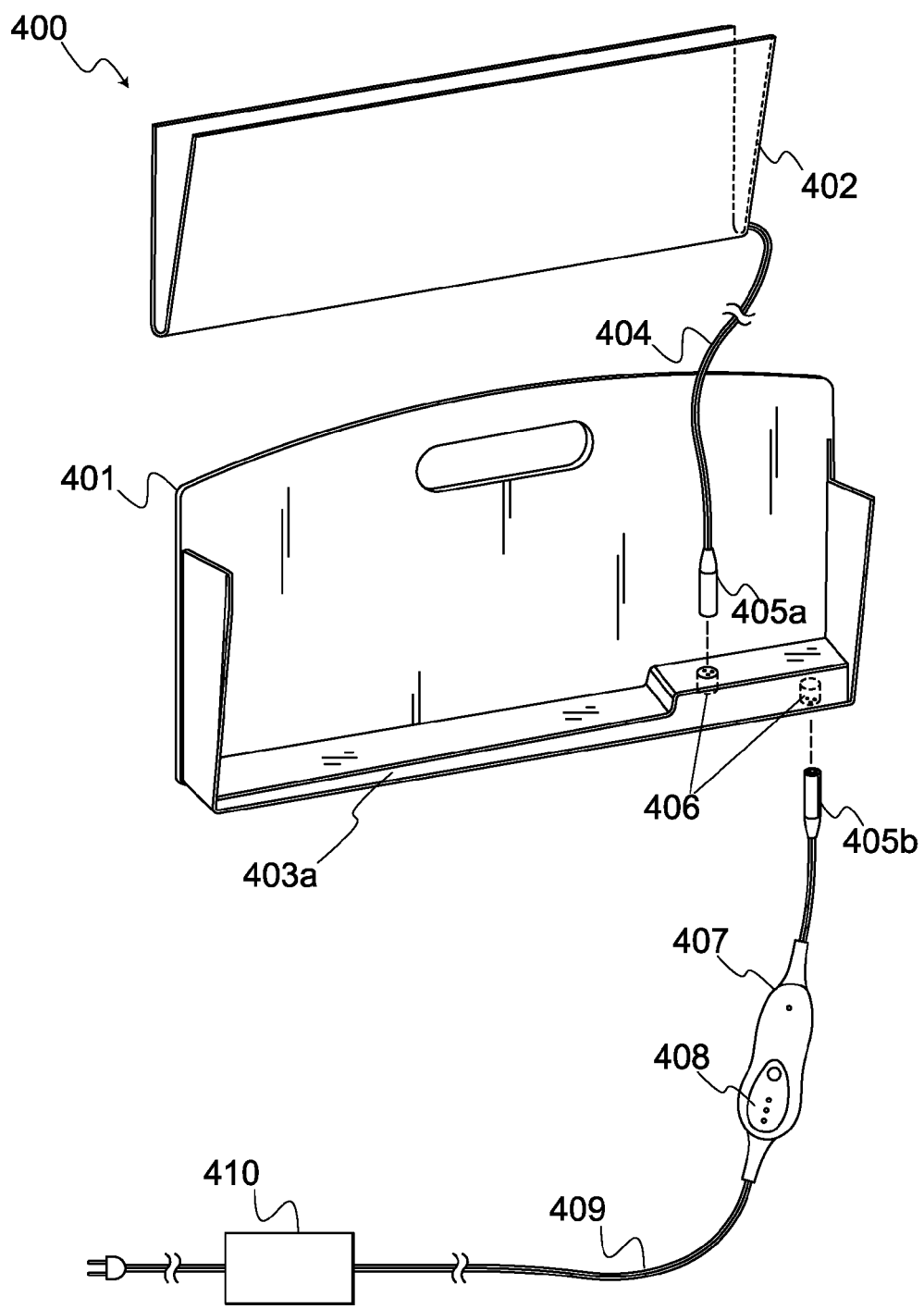
FIG. 4(a) depicts an exploded/cross-sectional view of an apparatus in accordance with an embodiment of the present invention, similar to that depicted in the diagram of FIG. 2.
Figure 4B:
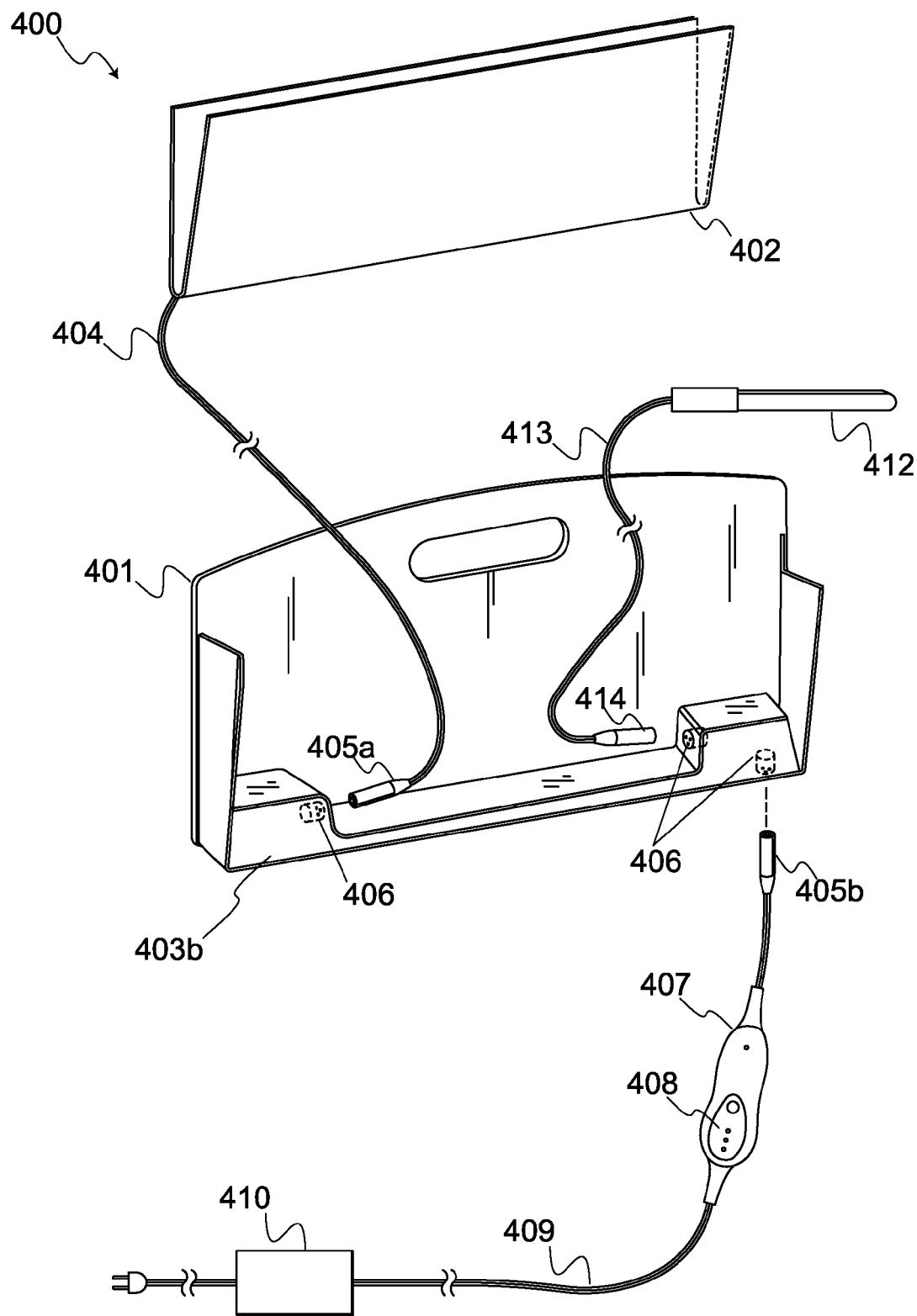
FIG. 4(b) depicts an exploded/cross-sectional view of an apparatus in accordance with another embodiment of the present invention, similar to that depicted in the diagram of FIG. 3.

Examples of possible embodiments of the present invention are shown in both FIG. 4(a) and FIG. 4(b). FIG. 4(a) depicts an exploded/cross-sectional view of an apparatus in accordance with an embodiment of the present invention, similar to that depicted in the diagram of FIG. 2. FIG. 4(b) depicts an exploded/cross-sectional view of an apparatus in accordance with another embodiment of the present invention, similar to that depicted in the diagram of FIG. 3.

Apparatus 400 is depicted in each figure, each figure showing a different embodiment therein. For example, both figures show apparatus 400 comprising outer housing or carrying case 401, inner housing or heating component 402, conduit or cable 404, connectors 405a, 405b and 406, control module 407, user interface 408, cord 409 and PSU 410. As explained above, these components provide for housing a heating element and providing a power supply to the heating element in order to warm an instrument that may be placed within carrying case 401, and control the desired temperature and operation of apparatus 400.

Interface 403a and interface 403b differ in that interface 403b allows apparatus 400 to warm more than one type of instrument. For example, and without deviating from the scope of the present invention, interface 403a provides power to a heating element in inside heating component 402. This type of configuration is desirable for instruments with surface areas that do not include a cavity. Examples of such instruments would include a vibrator or female stimulator. These devices have well known configurations and one of ordinary skill in the art will understand that those types of instruments do not typically include cavities; instead, vibrators or female stimulators typically have an outer surface area, which is designed to come into contact with one or more parts of the human body, such as an orifice, skin, or any other body part. Hence, a vibrator may be wrapped or snuggly secured inside heating component 402 in order to warm the instrument to a desired temperature.

Interface 403b further accommodates a power supply to another type of housing or heating element—a rigid housing or heating component 412. Heating component 412 may naturally include connectors, such as connector 414 for drawing power and, in some embodiments, communicating with a sensor (not shown). Heating component 412 includes a heating element configured to be inserted or registered with an instrument that has a surface area within a cavity of the instrument that will come into contact with a body part. An example of such instrument may include a male stimulator, such as a simulated vagina sex toy. A male stimulator also has well known configurations and one of ordinary skill in the art will understand that those types of instruments may typically include cavities with a surface area designed to come into contact with one or more parts of the human body. Hence, heating component 412 may be inserted into the cavity of the male stimulator in order to warm the instrument to a desired temperature.

In order to accommodate the one or more heating components (i.e. heating component 402, 412), interface 403a or 403b may include connection ports or connectors 406 to provide a connection means with cables or conduits 404 and 403 for heating components 402 and 412 respectively. If the control module of apparatus 400 is to be maintained externally to the device, one of the connectors 406 may be configured in an outer rim or edge of carrying case 401 in order to facilitate a connection when the carrying case is in a closed configuration (as shown in FIG. 1).

Figure 5A:
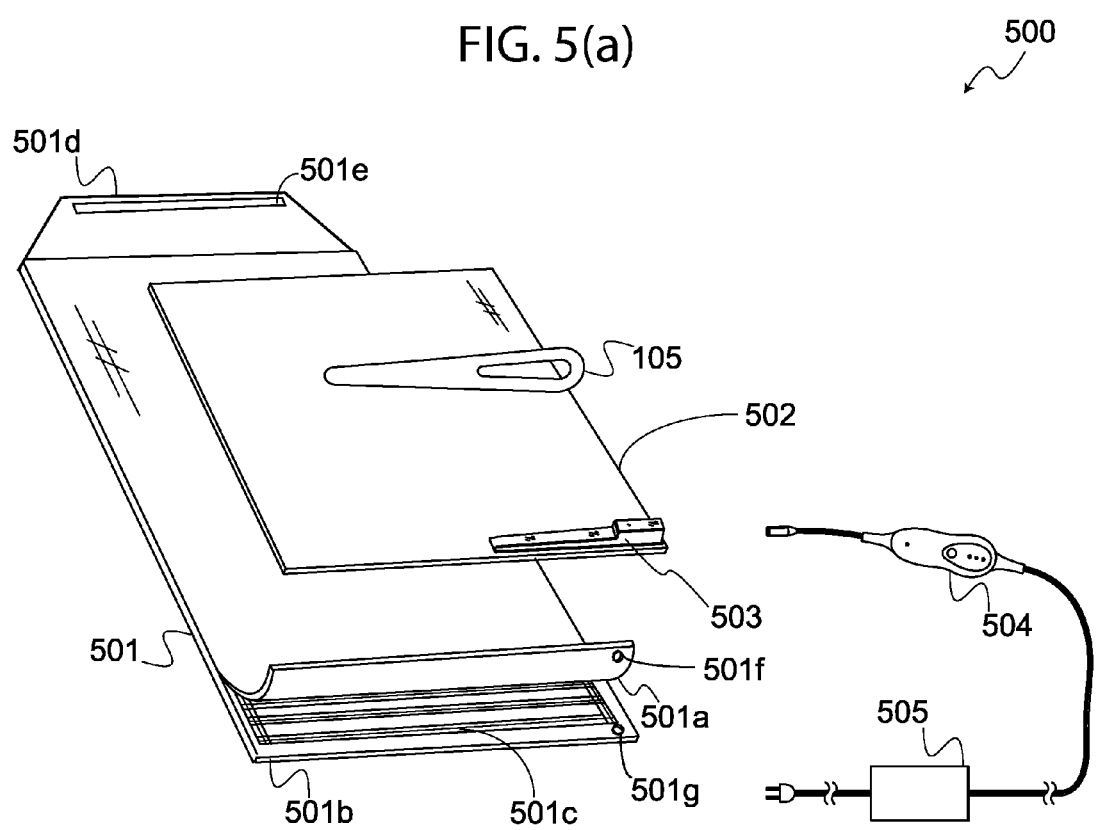
FIG. 5(a) depicts an exemplary embodiment of the present invention, comprising a flexible cover and a heating component, which may be rolled-up to contain one or more instruments.

Turning now to the next figure, FIG. 5(a) depicts an exemplary embodiment of the present invention, comprising a flexible cover and a heating component, which may be rolled-up to contain one or more instruments. Apparatus 500 comprises a different type of carrying means, including a flexible cover 501 in lieu of a hard housing such as housing 401. Apparatus 500 further includes heating component 502, interface 503, control module 504, and PSU 505.

Flexible cover 501 may be constructed of a wide variety of materials that may be folded, rolled, stretched or that are otherwise flexible. For example, and without deviating from the scope of the present invention, flexible cover 501 may be constructed of a polyurethane-polyurea copolymer, such as elastane or spandex, or may be constructed of latex, synthetic leather, leather, or any other natural or synthetic fibers that are durable and have some elastic qualities. Other well known materials may be used without deviating from the scope of the invention, including nylon, neoprene, or any other synthetic rubbers. Furthermore, flexible cover 501 may contain a single layer or multiple layers.

Multiple layers, for example layers 501a and 501b, may be desirable in some embodiments of the present invention, although it will become apparent that flexible cover 501 may comprise a single layer without deviating or limiting the scope of the present invention. In the shown embodiment, layers 501a and 501b enclose, contain or house another layer 501c. Layer 501c is typically a sturdier, yet flexible component that may add a structural component as well as a functional feature. For example, in some embodiments, layers 501a and 501b are constructed of similar materials such as a synthetic flexible material (e.g, synthetic leather, neoprene, spandex, etc.), while layer 501c may comprise a flexible ferrous mesh or metallic component. The metallic component of layer 501c is desirably flexible and elastic enough to be rolled up and stretched over instruments (i.e. discussed further below), but durable enough not to break apart. Furthermore, as stated above, layer 501c may be ferrous or metallic, or otherwise configured to be magnetically attracted with a magnetic component so as to add a means for holding flexible cover in a rolled-up position.

To further explain, as shown in the embodiment illustrated by FIG. 5(*a*), flexible cover 501 may include a protruding portion 501d at one of its extremities. Portion 501d further includes a magnetic component 501e. Magnetic component 501e may be stretched or placed over any area of flexible cover 501 and be magnetically attracted to layer 501 within surface 501. This magnetic attraction will securely attach portion 501d to surface 501 when surface 501 is rolled up for travel, to carry one or more instruments therein.

Of course, while layer 501c may be distributed throughout an entire interior of surface 501, as shown, layer 501c may merely comprise a small portion of surface 501. That is, layer 501c may be only at the opposite end of portion 501d or at any other location suitable to enable magnetic component 501e and layer 501c to connect and secure surface 501 in place. However, those skilled in the art will appreciate that one advantage to having layer 01c throughout an interior of surface 501 is that surface 501 may be secured from any point on surface 501. This feature would enable a wide size range of instruments to be rolled up within surface 501.

It should be apparent that other embodiments for securely holding surface 501 together are possible. For example, and without limiting the scope of the present invention, straps, buttons, zippers, draw strings, or any combination of features that facilitate secure containment and transportation of one or more instruments may be implemented. In one embodiment, rather than including magnetic component 501c, portion 501d may include any of the above-mentioned fasteners. Similarly, layer 501c may be absent from one embodiment of apparatus 500 altogether.

To conclude a discussion of surface 501, layers 501a and 501b may be constructed of the same material or may be different materials. For example, and without limiting the scope of the present invention, layer 501a may include a softer fabric while layer 501b may include a sturdier water resistant fabric such as nylon or polyurethane—suitable for providing a further measure of protection to any instrument within apparatus 500.

Heating component 502 may be similar to heating component 402. Heating component 502 is similarly flexible and is configured to be stretched, rolled-up and otherwise wrapped around one or more instruments such as instrument 105. Heating component 502 typically includes a heating element, which may include a sensor along with the heating element similar to the configuration of inner housing 202 shown in FIG. 2.

In alternative embodiments, heating component 502 may be differently configured, and rather than resemble a flat flexible surface, heating component 502 may comprise a substantially rigid component such as heating component 412. In such embodiment, interface 503 would be adapted to connect with a connector for the component or probe. As mentioned above, such embodiment for heating component 502 may be desirable for using with differently shaped tools that include a surface area within a cavity that may be desirable to warm. Utilizing a probe or rigid housing such as that of heating component 412 may be advantageous to properly radiate heat to certain objects.

In order to draw power and or communicate with one or more sensors (i.e. in some embodiments) heating component 502 includes an interface 503. Interface 503 is configured to provide power to a heating element within heating component 502, which in turn generates a source of heat that will radiate, for example, to instrument 105. Interface 503 may be configured to connect with control module 504 in any desirable configuration, and directly or through one or more openings on flexible cover 501, such as openings 501g, 501f. Alternatively, interface 503 may have connectors or connection means that are interior or exterior to flexible cover 501, without deviating from the scope of the present invention. Furthermore, interface 503 may be configured to couple to one or more heating components in a similar fashion as the embodiment shown in FIG. 4(*b*).

Control module 504 and PSU 505 provide a user with an easy means to connect apparatus 500 to a power supply, and control the heat output for warming instrument 105. Control module 504 may include circuitry that may range or vary in complexity; may comprises a controller, memory, and user interface similar to the control modules for the embodiments described above. Control module 504 may be the control center for apparatus 500 and is typically situated outside of flexible cover 501 as shown. Control module 504 facilitates control of the temperature output of the heating element within surface 501, allowing a user to turn the device on or off, and either setting the device to a pre-set temperature or manually setting the temperature via a user input. Typically control module 504 draws power from PSU 505 and supplies an adequate voltage to heating component 502. Furthermore, control module 504 may communicate with one or more sensors in order to maintain the instrument at a desired temperature, and as previously described, these components of apparatus 500 may be more or less complex without deviating from the scope of the invention.

One advantage of apparatus 500 is that its configuration allows for a wide range of sizes and shapes of instruments to be warmed and carried by the device. While instrument 105 may be a light slim instrument, other instruments may be bulkier in shape. Even though a hard carrying case such as carrying case 101 may be limited to one instrument or object if the instrument or object is bulky, apparatus 500 may easily hold the bulkier object or instrument, perhaps along with instrument 105, since flexible cover 501 may be stretched and wrapped around or rolled up over the instruments or objects.

Figure 5B:
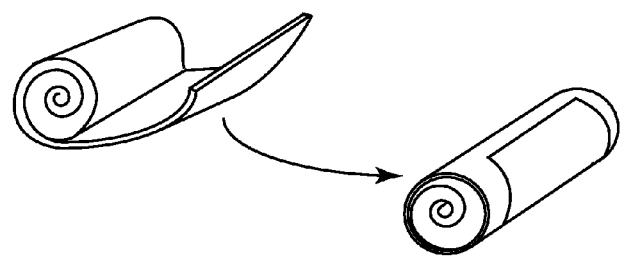
FIG. 5(b) depicts the exemplary embodiment illustrated in FIG. 5(a) in a rolled-up configuration readied for travel.

FIG. 5(b) illustrates the exemplary embodiment depicted in FIG. 5(a) in a rolled-up configuration. More specifically, FIG. 5(b) shows how apparatus 500 may be rolled up to securely contain one or more instruments. As shown, similar in motion to rolling up a towel, a user may place instrument 105 atop heating component 502 and roll-up surface 501 and heating component 502 into a single roll. In an exemplary embodiment, portion 501d is configured to magnetically couple with layer 501c within surface 501. In other embodiments, portion 501d is configured to fasten with or otherwise securely connect to surface 501 by any variety of connecting means. For example and without deviating from the scope of the present invention, portion 501d may include straps, buttons, zippers, draw strings, hook-and-loop fasteners (e.g. Velcor®), or any combination of features, fasteners, or connectors that facilitate secure containment and transportation of one or more instruments.

Figure 6A:
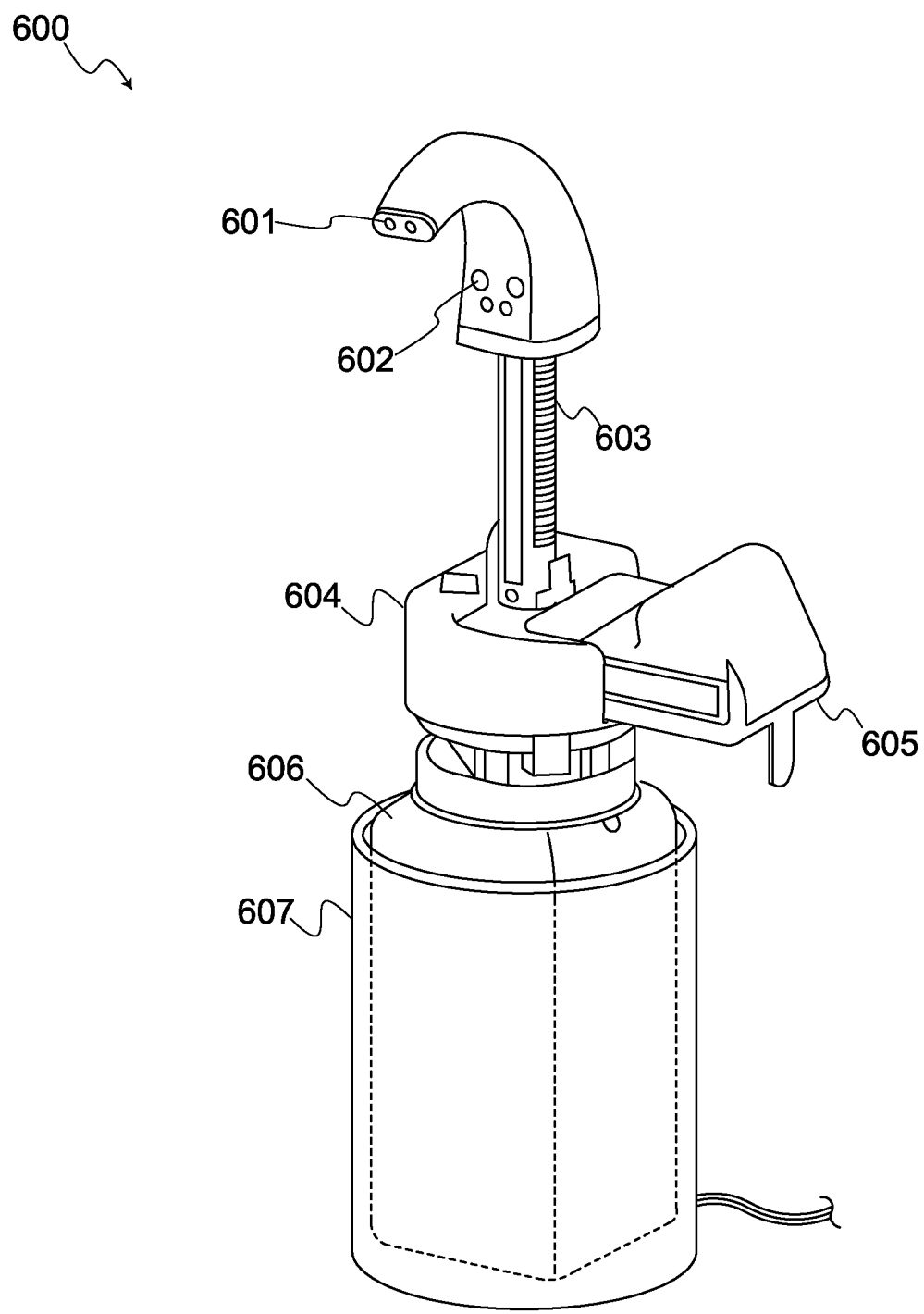
FIG. 6(a) depicts another device in accordance with the present invention, which comprises a heating element designed to warm a container for supplying a fluid that may be used in conjunction with an instrument, or prior to its use.
Figure 6B:
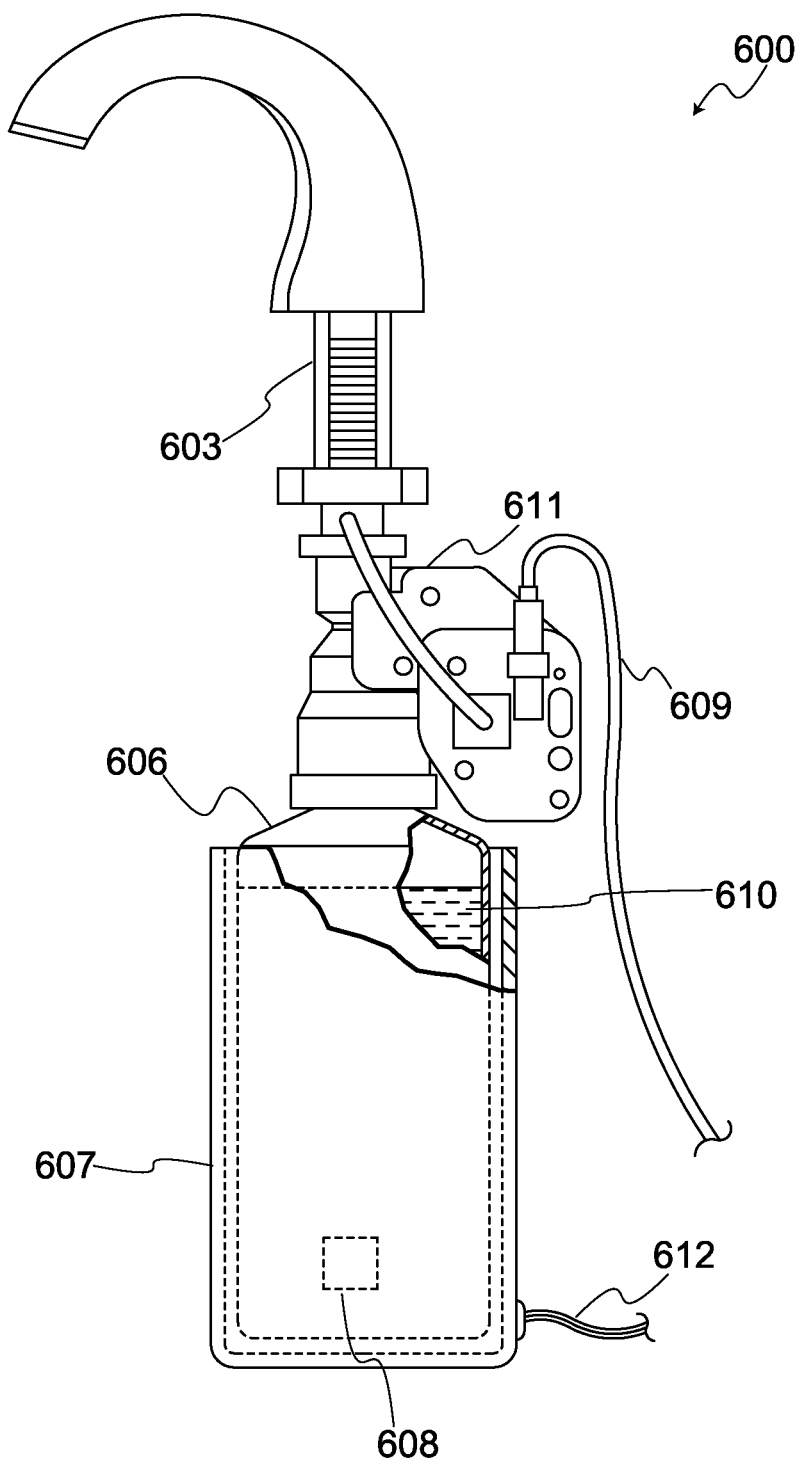
FIG. 6(b) depicts a cross-sectional view of the device depicted in FIG. 6(a).

Turning now to the last two figures, FIG. 6(a) depicts another device in accordance with the present invention, which comprises a heating element designed to warm a container for supplying a fluid that may be used in conjunction with an instrument, or prior to its use. FIG. 6(b) depicts a cross-sectional view of the device depicted in FIG. 6(a). More specifically, FIG. 6(a) and FIG. 6(b) show an electrically heated vessel, or apparatus 600, in accordance with an exemplary component for a system of the present invention.

Apparatus 600 typically includes a body or base 607, which is configured to receive a fluid container or vessel 606. Base 607 includes a cavity for housing a heating element and a temperature sensor. A resistive circuitry embedded within base 607 provides the heating element that generates a desired temperature for warming a fluid inside vessel 606.

A control module (not shown), similar to control module 407, may be connected to the circuitry, and in communication with thermo sensor 608. The circuitry thus provides a means to control the desired temperature of the fluid inside the fluid container or vessel 606. Vessel 606 may be a simple fluid container, or a motorized sensor activated fluid container, as shown.

In such an embodiment, wherein apparatus 600 includes a motorized and sensor activated fluid container, apparatus 600 further comprises nozzles 601, motion sensors 602, output stem 603, pump housing 604, motor housing 605 and motor 611, conduits 609, 612, and fluid 610. Nozzles 601 expel fluid 610 upon actuation of motor 611, which activates a pump within pump housing 604 once a user's hands or movement thereof is detected by motion sensors 602. Output stem 603 guides fluid 610 out of vessel 606 when apparatus 600 is activated. Motor 611 is powered from a power supply via conduit 609. Similarly, conduit 612 delivers power to the heating element within base 607. Once placed within base 607, vessel 606 may be warmed or heated so that fluid 610 is expelled at a desired temperature.

Apparatus 600 may be a complementary component of apparatus 600 and form part of a system of warming instruments. For example, and without deviating from the scope of the present invention, where apparatus 400 is utilized to warm instruments for use during sexual activities, apparatus 600 may supply a fluid consisting of a lubricating substance to facilitate the use of the warmed instruments. Similarly, where apparatus 400 is utilized to warm instruments or objects used during medical procedures, for example speculums used during gynecological exams; apparatus 600 may supply a warm fluid to alleviate any discomfort caused by insertion of the speculum at room temperatures.

In practice, this system facilitates the warming or heating of instruments to a desirable temperature so as to make their use a more pleasant experience. The system effectively prevents undesirable interruptions that may be caused by the discomfort of experiencing a temperature differential when the instrument comes in contact with the body. In exemplary embodiments, the transportable apparatus comprising one or more heating elements may be an electrically heated carrying case or flexible cover, for transporting instruments in a discrete and sanitary manner, which prepares the instruments for use by warming or heating to a desired temperature. In such embodiment, the electrically heated vessel for containing a fluid to be used in conjunction with the instruments may also be provided as part of a system that facilitates the comforting use of the instruments.

In addition to the examples of instruments that may be warmed/prepared for use during sexual activities, other objects for other activates may similarly be prepped for increase comfort. For example, medical instruments that may need to be inserted, such as speculums may be warmed prior to insertion; therapeutic stones that are often heated and placed on the body may be carried and warmed using the system. Moreover, the instruments or objects may be carried in a sanitary manner prior to their use so as to ensure a comforting and hygienic experience.

An apparatus and system for heating instruments has been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

What is claimed is:

1. An apparatus for warming adult toys, comprising:
    a carrying case including a handle on a top portion of the carrying case, the carrying case configured to transport and contain a plurality of adult toys;
    a first heating component removably coupled to the interior of the carrying case comprising:
        a substantially flat flexible surface area configured to wrap around a first adult toy,
        a first cable for transmitting power to the first heating component, and
        a first connector configured to removably connect the first cable to the interior of the carrying case;
    a second heating component removably coupled to the interior of the carrying case comprising:
        a rigid housing configured to register with a cavity of a second adult toy,
        a second cable for transmitting power to the second heating component, and
        a second connector configured to removably connect the second cable to the interior of the carrying case;
    an interface configured to simultaneously warm the first and second adult toys secured in an interior bottom portion of the carrying case, the interface including:
        a first connector port configured to receive the first connector of the first heating component, a second connector port configured to receive the second connector of the second heating component, wherein the second connector port is situated opposite to and facing the first connector port, a third connector port situated below the first and second connector ports in an outer edge of the carrying case, and circuitry configured to supply power to the first and second heating components; and a control module configured to removably connect to the third connector port and supply power to the circuitry.

2. The apparatus of claim 1, wherein the first heating component further comprises an insulating soft linen layer adapted to insulate and preserve the first adult toy.

3. The apparatus of claim 1, wherein the interface for connecting the heating components to a power supply is configured to receive sensor data from one or more sensors situated within the first and second heating components.

4. The apparatus of claim 3, wherein the control module further comprises a user interface for controlling the heat output generated by the heating components.

5. The apparatus of claim 3, wherein the control module is configured to:

receive the sensor data from the one or more sensors situated within the first and second heating components; and execute an executable program stored in a memory of the control module for controlling the temperature output of the first and second heating components.

\* \* \* \* \*